(12) United States Patent
Poulsen

(10) Patent No.: US 9,168,057 B2
(45) Date of Patent: Oct. 27, 2015

(54) SURGICAL APPARATUS

(75) Inventor: Henrik Bisgaard Poulsen, Slangerup (DK)

(73) Assignee: KEBOMED AG, Zug (CH)

( * ) Notice: Subject to any disclaimer, the term of this patent is extended or adjusted under 35 U.S.C. 154(b) by 165 days.

(21) Appl. No.: 12/836,957

(22) Filed: Jul. 15, 2010

(65) Prior Publication Data

US 2012/0016399 A1 Jan. 19, 2012

(51) Int. Cl.
*A61B 17/32* (2006.01)
*A61B 17/3207* (2006.01)
*A61B 17/3211* (2006.01)
*A61B 17/3205* (2006.01)
*A61B 17/34* (2006.01)
*A61B 17/00* (2006.01)

(52) U.S. Cl.
CPC ... *A61B 17/320758* (2013.01); *A61B 17/32002* (2013.01); *A61B 17/320016* (2013.01); *A61B 17/32053* (2013.01); *A61B 17/3421* (2013.01); *A61B 17/3496* (2013.01); *A61B 2017/0023* (2013.01); *A61B 2017/00734* (2013.01); *A61B 2017/320072* (2013.01); *A61B 2017/32113* (2013.01); *A61B 2017/320775* (2013.01)

(58) Field of Classification Search
CPC ............ A61B 17/32; A61B 17/32002; A61B 17/320016; A61B 17/320758; A61B 17/34; A61B 2017/32113; A61B 2017/320072; A61B 2017/0023; A61B 2017/00734; A61B 2017/320775; A61B 17/32053; A61B 17/3412; A61B 17/3496

USPC ......... 606/119, 125–127, 167, 168, 170, 172, 606/180, 185; 600/562–564; 227/67
See application file for complete search history.

(56) References Cited

U.S. PATENT DOCUMENTS

| | | | | |
|---|---|---|---|---|
| 4,108,182 A | * | 8/1978 | Hartman et al. | 606/171 |
| 4,796,624 A | * | 1/1989 | Trott et al. | 606/185 |
| 5,814,044 A | | 9/1998 | Hooven | |
| 5,879,358 A | | 3/1999 | Semm | |
| 5,916,198 A | | 6/1999 | Dillow | |
| 5,957,888 A | * | 9/1999 | Hinchliffe | 604/117 |
| 6,039,748 A | | 3/2000 | Savage et al. | |
| 6,245,084 B1 | * | 6/2001 | Mark et al. | 606/167 |
| 7,549,972 B2 | * | 6/2009 | Luloh et al. | 604/22 |
| 8,100,928 B2 | * | 1/2012 | Nohilly et al. | 606/180 |
| 8,216,246 B2 | * | 7/2012 | Luloh et al. | 606/107 |
| 2004/0066008 A1 | * | 4/2004 | Smith | 277/628 |
| 2005/0171504 A1 | * | 8/2005 | Miller | 604/506 |
| 2007/0270790 A1 | * | 11/2007 | Smith et al. | 606/32 |
| 2008/0039884 A1 | | 2/2008 | Nohilly | |
| 2008/0255597 A1 | * | 10/2008 | Pravong et al. | 606/169 |

FOREIGN PATENT DOCUMENTS

WO  WO 2009/036875 A1  3/2009

* cited by examiner

*Primary Examiner* — Ryan Severson
*Assistant Examiner* — Rachel S Papeika
(74) *Attorney, Agent, or Firm* — Muncy, Geissler, Olds & Lowe, P.C.

(57) ABSTRACT

A single use morcellator utilizes a disposable housing, cutting tube, battery and motor in combination with an attached and adjustable trocar to enable the surgeon to selectively utilize the cutting edge of the tube. The battery and control circuit are completely contained within the integral morcellator such that no separate components are needed.

12 Claims, 3 Drawing Sheets

SURGICAL APPARATUS

BACKGROUND OF THE INVENTION

The present invention relates to the field of surgery and more particularly to a surgical instrument to be used in gynecologic surgery and urological surgery and in other surgical fields. One of the most well-known procedures in the gynecology field are hysterectomies where the uterine body is removed. The advantages by doing the procedure laproscopicly are that the patient on needs two or 3 minor scar on the abdomen, and potentially has an easier recovery than when the abdominal muscle is cut in older forms of surgery. Once the uterus has been separated from the cervix the uterine tissue need to be removed from the patient throughout one of small incisions in the abdomen. Since the uterus has a diameter up to 300 mm or more a appropriate tool is need to render the uterus into pieces sized in a way that they can be removed throughout one of the small incisions. The tool to do this is called a Morcellator. The morcellator renders the tissue into small pieces or preferably long strips which can be drawn out through the central lumen of the morcellator. Most of the morcellators uses a principle where a rotating sharp tube cuts into the uterus while the surgeon pulls the tissue backwards using an appropriate forceps.

The common morcellator is built from following basic parts:

Cutting tube, which is a driven rotating tube operating from 200 to 1000 RPM depending on brand/model, and which can be made from stainless steel or mild steel. The wall thickness vary such that for reusable blades relatively thick wall blades are often seen while single use blades tend to be made from thin wall steel.

Drive Unit:

The drive unit can be located in hand-piece or in a separate "drive unit" placed on the table away from the hand-piece. The separate drive unit can have a built in motor turning the cutting tube via a gearbox or a motor may be connected the gearbox through a mechanical cable extending from a remote drive or it can be a power supply feeding the motor in the hand-piece with electrical power.

Gear Box:

The drive unit can be a separate unit from the drive unit and is typically intended to transfer the torque from the motor to the rotating cutting tube.

Control Mechanism.

Various mechanisms are known in the prior art with the most common being a foot pedal connected to the drive unit and acting as an on/of switch for the morcellator. A few powered morselators are hand controlled operated and do not have a foot pedal.

Hand Piece:

The prior art hand pieces for powered morselators range from bulky to heavy.

Charging Stands and Power Supplies:

Prior art morcellators have been powered by remote and encased power supplies that were either renewable or rechargeable.

Previous morsellators were cumbersome could not deliver adequate functional capabilities unless they were driven by an external or rechargeable power supply. For example one widely used morsellator uses a remote drive which was connected to the cutting tube through a cable which extended from the sterile operating field to a rotary drive. As noted above this device could be controlled by a foot control connected to the rotary drive. None of the known powered morsellators are unitary integrated devices which are designed to be disposed of after a single use. Some may have disposable components such as a cutting tube, however the remaining parts are all parts that must be tediously sterilized and cleaned after each use, thereby increasing the labor cost of the medical services. If any component accidentally leaves the sterile operating field, the procedure must be halted until a new sterile replacement for the component can be obtained from supply. Likewise, should a component such as a drive cable become tangled during the course of a procedure, the surgeon's control of the morsellator is compromised by the tension in the cable and the procedure must be stopped and restarted with a replacement part. It is noteworthy to mention that some surgeons consider the driven morsellator the most dangerous surgical instrument in use today. Consequently a need exists for a ready to use, disposable, single piece morsellator that will be smaller and more ergonomic than existing morsellators.

SUMMARY OF THE PRESENT INVENTION

It is an object of the present invention to provide a fully integrated, one piece, disposable morcellator to be used for the surgical gynecological and urological field. The fully disposable morcellator offers the surgeon several advantages including ease of use, no parts to be cleaned, and full control by the hand with high level of safety in combination with excellent maneuverability.

These and other objects and advantages of the invention will become apparent from the following detailed description of the preferred embodiment of the invention.

BRIEF DESCRIPTION OF THE DRAWINGS

An apparatus for tissue removal is depicted in the accompanying drawings which form a portion of this disclosure and wherein.

DESCRIPTION OF THE PREFERRED EMBODIMENT

Figure 1:
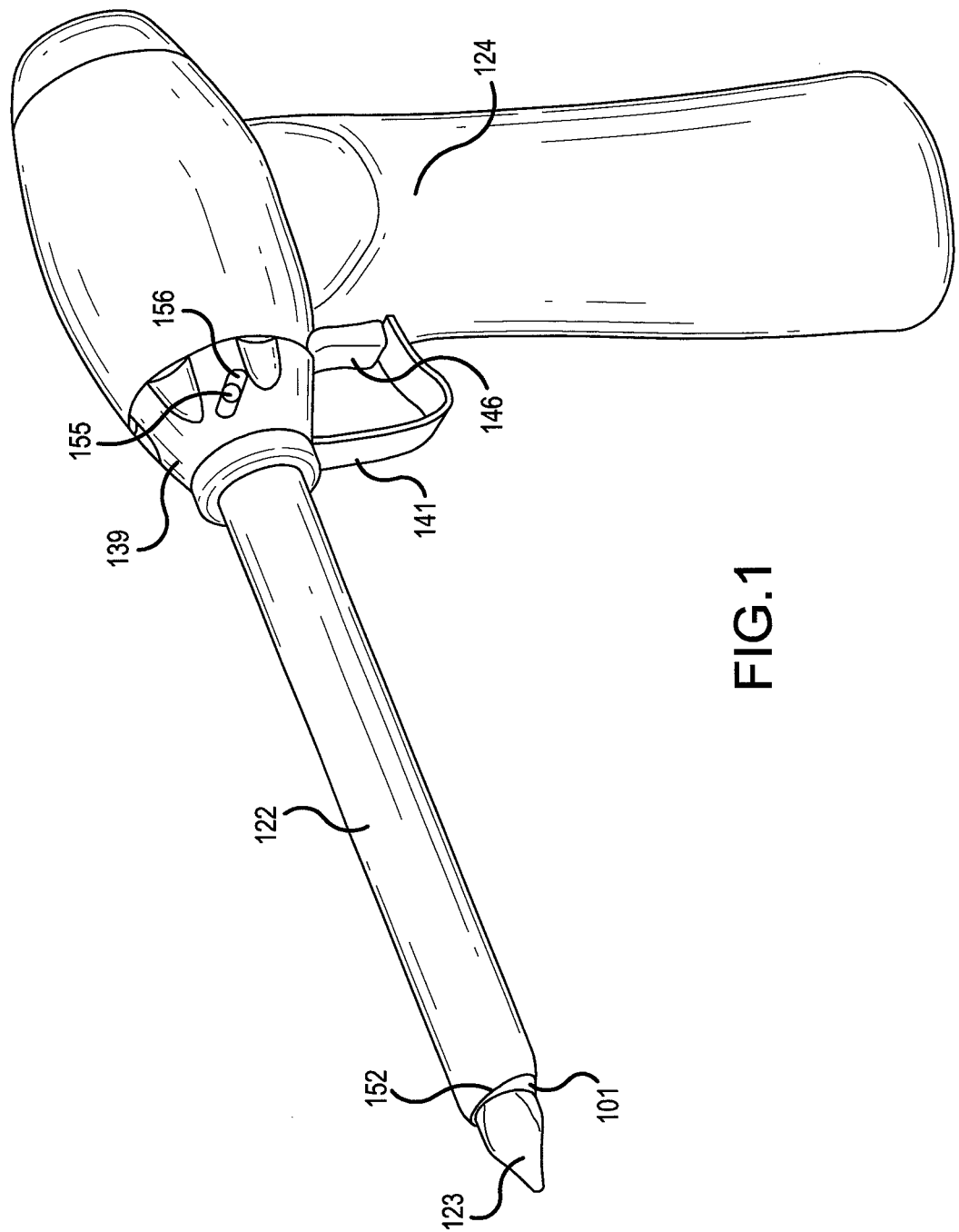
FIG. 1 is a perspective view of the integrated morsellator.

Referring to the FIGS. 1-4 for a clearer understanding of the invention, it may be seen that the preferred embodiment of the invention contemplates a fully disposable morcellator 11. Morcellator 11 includes a tubular cutting tube 101 which extends from a pistol grip type plastic housing 124 and defines a lumen 102 there through. Housing 124 contains an alkaline battery package 112 powering an enclosed motor 113. The motor 113 drives a toothed wheel or gear 114 which engages a second gear 103 formed on a radial extension 104 of a hub 106 as a part of the 90 degree gear 115 which rotates the cutting tube 101. Hub 106 includes an elongated tubular portion 107 within which cutting tube 101 is received and secured and radial extension 104. Cutting tube 101 is made from thin wall stainless steel or other acceptable metallic tube and is ground at the distal end to be as sharp as possible. Hub 106 is preferably made from plastic, thus the two parts are mechanically joined together with any suitable means such as fasteners or an adhesive that prevents any longitudinal or annular displacement between the two parts. Plastic includes any rigid polymer that will hold the cutting tube in place despite longitudinal forces applied to it during the surgery. It will be understood that any other suitable means of joining the cutting tube to the hub may be employed however, the tube must not be displaced longitudinally in the hub during use. The secured end of hub 106 is also fitted with a sealing device such as a duckbill housing 125 which is rigidly secured to housing 124. The duckbill housing 125 avoids or minimizes gas leakage during the procedure. The duckbill house encompasses a duckbill seal 127 and a sealing disc 128. The duckbill seal 127 stops gas leakage when no forceps or instrument are inserted through the lumen 102 of the morcellator and the disc 128 stops leakage when the forceps are inserted through the lumen 102.

Hub 106 is rotatably mounted within housing 124 on a bearing 131 supported on gussets 132 such that the hub 106 and thus the cutting tube 101 are restrained from axial movement. A seal 133 prevents leakage about the hub 106 at bearing 131. The opposite end of hub 106 is mounted for rotation on bearing 136 in flange 137 on duckbill housing 125 such that lumen 102 is in communication with the interior of duckbill housing 125.

The morcellator 11 includes a built in trocar 122 which means that the morcellator in companion with the obturator 123 can be introduced through an incision without the necessity of a separate trocar. Trocar 122 is rotatably mounted to housing 124 such that by rotating trocar 122 it is movable axially along cutting tube 101 to cover more or less of the sharp distal end of the cutting tube 101. Preferably, trocar 122 can be adjusted using integral knob 139 to at least three positions. In the SAFE position the trocar completely shields the cutting tube 101 and the morcellator is safe and ready to be introduced through the incision in the abdomen, Cut 1 exposes the cutting edge of cutting tube 101, and Cut 2 retracts the trocar such that only an arc of the cutting edge is exposed. Preferentially, knob 139 is selectively turned to each position and is retentively held at that position by a detent and ball or other locking mechanism. In one embodiment, the trocar 122 and knob cooperate with a trigger guard 141 which is attached to housing 124 below a trigger switch 146 and extends outwardly to a free end 142 which engages slots in knob 139. To rotate the trocar 122 the trigger guard end 142 is disengaged and then re-engaged in a selected slot 143. The longitudinal movement of the trocar 122 is created by the interaction of the knob 139 with a cam surface such as a protusion 155 formed on housing 124 and engaged in a slot 156 in knob 139. Various other camming combinations are contemplated.

As will be seen in FIG. 1, the distal end 152 of trocar 122 is beveled and angled such that one side of the end of the trocar forms an ellipse with the result that one side of the trocar is shorter than the other. As a result, one side of cutting tube 101 can be exposed without exposing the entire end of cutting tube 101. This feature enables the longitudinal movement of trocar 122 to selectively expose the cutting tube 101. The partial setting, or Cut 2 setting, is to be used when the surgeon wants to use the morcellator to engage the uterus at a selective area on the cutting tube. At the partial setting the sharp end of the cutting tube is partly shown. The Cut 1, or full, setting fully exposes the cutting edge of the cutting tube and is used when the surgeon wants to core out strips of tissue.

Figure 2:
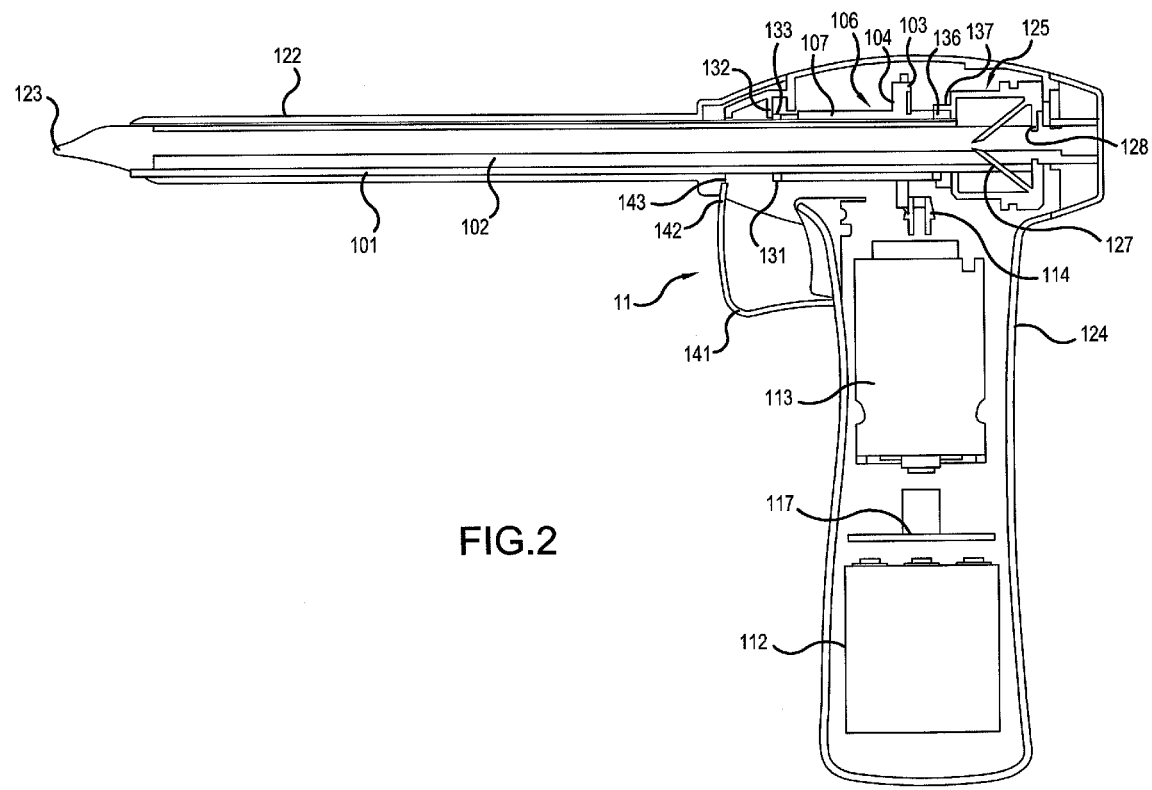
FIG. 2 is a side sectional view of the integrated morsellator.
Figure 3:
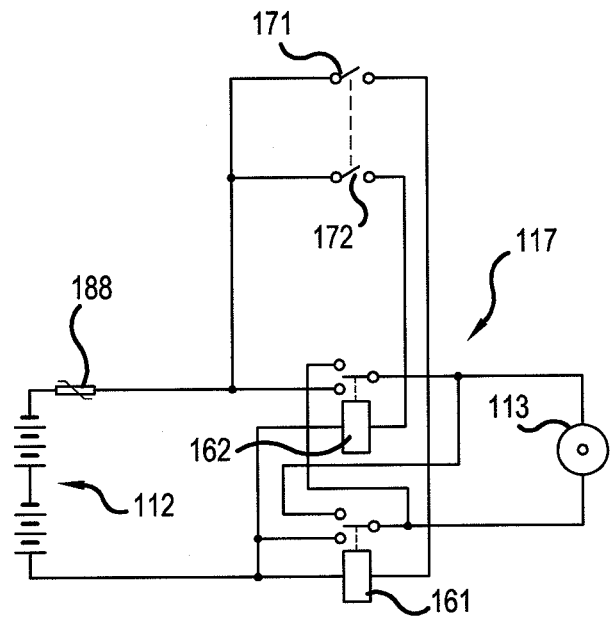
FIG. 3 is a schematic diagram of the control circuit of the morsellator.
Figure 4:
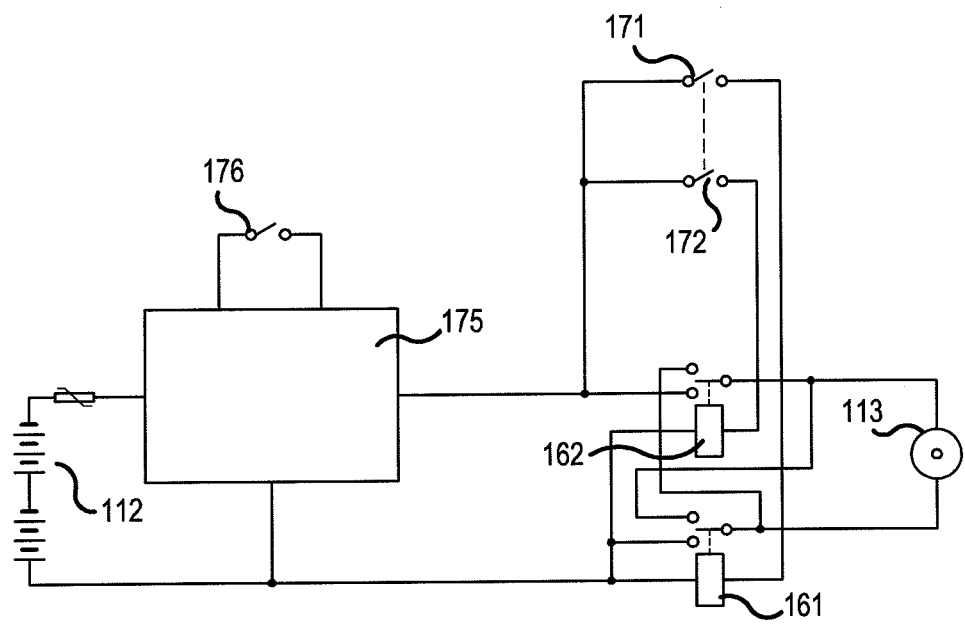
FIG. 4 is a schematic diagram of another embodiment of the control circuit.

The battery package 112 and motor 113 are electrically connected through a printed circuit board 117. Trigger 146 is mechanically coupled connected to two switches 171 and 172 which should have be functionality equivalent to a B3S-1002P. Referring to FIGS. 2 to 4, the battery package 112 is preferably a 9V single use battery package including six 1.5V 2500 mAH batteries connected in series connected with a overload protecting fuse or diode 188 such as an S175. It will be appreciated that any suitable battery can be used. The battery package is wrapped in plastic (shrink tube) and fitted with 0.5 mm$^2$ leads.

The relays 161 and 162 on the PCB are miniature power PCB relays such as RY211009. The motor is connected to the battery through a normally open contact in each of the relays such that both relays have to be activated to close the contacts and power the motor. The other contacts in there relays are normally closed and cross connected such that when the trigger 146 is released and switches 171 and 172 are opened the two poles on the motor are short circuited through the relay contacts. By short circuiting the two motor poles the motor stops immediately when the trigger is released. Unloaded the motor has a speed of about 5800 RPM and after the gearing the rotating tube has a speed of about 650 RPM.

As seen in FIG. 4 the voltage across the motor can be increased to give two speed operation using voltage booster 175. A boost switch 176 can be separately actuated or can be incorporated as a second level of the depression of trigger 146.

The apparatus as described and illustrated is intended for one use on one patient and is not intended to be sterilized or reused, thus, the cutting tube is not replaceable or interchangeable and the batteries are not replaceable or rechargeable. However, the design is sufficiently light weight and compact as to allow the surgeon to comfortably manipulate the instrument during the procedure without cumbersome cords or drive cables. It is to be understood that the form of the invention shown is a preferred embodiment thereof and that various changes and modifications may be made therein without departing from the spirit of the invention or scope as defined in the following claims.

What is claimed is:

1. A single use, disposable apparatus for removing tissue from within a living body comprising:
   an ergonomic grip adapted to be held in a surgeon's hand;
   a hollow cylindrical tube defining a lumen therethrough, the cylindrical tube being mounted in said grip for driven rotation about its longitudinal axis, and having a distal end defining an annular blade;
   a hub including an elongated tubular portion within which the cylindrical tube is received and secured, the hub being provided with a sealing device which is rigidly secured to the housing and preventing leakage through the lumen when no instrument is inserted through the lumen;
   a trocar surrounding said cylindrical tube and supported by said grip for selective longitudinal movement between a first position covering said annular blade, a second position exposing all of said annular blade and a third position exposing an arc of said annular blade;
   a motor mounted within said grip and connected to said cylinder for controlled rotation thereof;
   a battery contained within said grip and connected to power said motor;
   a switch connected between said battery and motor for selectively energizing said motor;
   a cam surface formed on said grip proximal and cooperative with said trocar such that rotation of said trocar about said cylindrical tube cams said trocar between said positions; and
   a plurality of annularly spaced slots formed on said trocar proximal said grip and a locking member formed on said grip for selectively engaging one of said slots to selectively fix said trocar in relation to said cam surface,
   wherein the entire apparatus is disposable after a single use, wherein the switch effects an immediate stopping of the motor by short circuiting two poles of the motor, and wherein said locking member is a guard for said switch which is selectively movable into engagement with one of said plurality of recesses.

2. The apparatus as described in claim 1, wherein said trocar can be selectively fixed in at least one of said first, second and third positions.

3. The apparatus as described in claim 1, wherein said switch is connected between said motor and said battery so as to connect opposing wiring in said motor to prevent rotation of said motor when said motor is not energized through said switch.

4. The apparatus as described in claim 1, wherein said cylindrical tube is captured within a drive sleeve including a first annular gear in cooperative engagement with a second gear mounted for rotation on an output shaft from said motor, said drive sleeve restrained from axial motion within said grip.

5. The apparatus as defined in claim 1, wherein said cylindrical tube selectively receives an obturator there through such that said obturator extends beyond said trocar.

6. The apparatus according to claim 1, wherein said trocar is configured to be selectively fixed in said first position, said second position and said third position.

7. The apparatus according to claim 6, wherein said trocar is configured to be selectively and rotationally fixed in said first position, said second position and said third position.

8. The apparatus according to claim 1, wherein said trocar is selectively movable between the first position, the second position and the third position by rotation of the trocar.

9. A disposable surgical tool for removing tissue from with a living organism through a small incision comprising in combination:

an elongated cylinder defining a lumen therethrough, the cylinder having a first end sharpened to form a cutting edge;

a hub including an elongated tubular portion within which the cylinder is received and secured, the hub being provided with a sealing device which is rigidly secured to the housing and preventing leakage through the lumen when no instrument is inserted through the lumen;

a trocar mounted coaxially with said cylinder and movable longitudinally to selectively expose said cutting edge for selective engagement with tissue to be cut, expose an arc of said cutting edge or covering said cutting edge;

a housing adapted to be held in one hand of a surgeon supporting said elongated cylinder for rotation about the longitudinal axis of said cylinder and supporting said trocar for selective linear movement along said cylinder, said housing providing access to the interior of said cylinder for removal of tissue there through;

a motor mounted in said housing for selectively rotating said cylinder;

a. battery mounted within said housing and operably connected to supply power to said motor;

a switch mounted on said housing and electrically connected between said motor and said battery so as to connect opposing wiring in said motor to prevent rotation of said motor when said motor is not energized through said switch;

a cam surface formed on said housing proximal and cooperative with said trocar such that rotation of said trocar about said cylinder cams said trocar between said positions; and a plurality of annularly spaced slots formed on said trocar proximal said housing and a locking member formed on said housing for selectively engaging one of said slots to selectively fix said trocar in relation to said cam surface, wherein said surgical tool is intended for a single use, wherein the switch effects an immediate stopping of the motor by short circuiting two poles of the motor, wherein said locking member is a guard for a human actuable switch for controlling said morcellator, wherein said guard is selectively movable into engagement with one of said plurality of slots.

10. The apparatus as described in claim 9, wherein said trocar can be selectively fixed in a first position exposing the arc of said cutting edge, a second position exposing all of said cutting edge and a third position exposing none of said cutting edge.

11. The apparatus as described in claim 9, wherein said cylinder is captured within a drive sleeve said drive sleeve being restrained from axial motion within said housing.

12. The apparatus as defined in claim 9, wherein said cylinder selectively receives an obturator there through such that said obturator extends beyond said trocar.

* * * * *